(12) United States Patent
Selner

(10) Patent No.: US 7,243,444 B2
(45) Date of Patent: Jul. 17, 2007

(54) ATHLETIC FOOTWEAR AND THE LIKE WITH INTEGRAL SUPINATOR DEVICE

(75) Inventor: Marc Selner, 4335 Laurel Canyon Dr., Studio City, CA (US) 91604

(73) Assignee: Marc Selner, Tarzana, CA (US)

( * ) Notice: Subject to any disclaimer, the term of this patent is extended or adjusted under 35 U.S.C. 154(b) by 42 days.

(21) Appl. No.: 10/865,290

(22) Filed: Jun. 10, 2004

(65) Prior Publication Data

US 2005/0274045 A1    Dec. 15, 2005

(51) Int. Cl.
*A43B 7/20*    (2006.01)
(52) U.S. Cl. .................. 36/89; 36/28; 36/144; 36/68
(58) Field of Classification Search ............. 36/89, 36/92, 68, 69, 27, 37, 28, 144, 170
See application file for complete search history.

(56) References Cited

U.S. PATENT DOCUMENTS

| | | | |
|---|---|---|---|
| 1,572,213 A | 2/1926 | Lucas | |
| 3,861,399 A | 1/1975 | Huff | |
| 4,187,620 A | 2/1980 | Selner | ............. 36/28 |
| 4,313,433 A | 2/1982 | Cramer | |
| 4,377,041 A | 3/1983 | Alchermes | |
| 4,392,487 A | 7/1983 | Selner et al. | ............. 128/80 H |
| 4,446,633 A | 5/1984 | Scheinhaus et al. | ......... 36/11.5 |
| 4,510,701 A * | 4/1985 | Schour et al. | ............. 36/68 |
| 4,649,939 A * | 3/1987 | Curtis | ............. 602/27 |
| 4,753,228 A | 6/1988 | Selner et al. | ............. 128/80 R |
| 4,759,136 A * | 7/1988 | Stewart et al. | ............. 36/114 |
| 4,766,681 A * | 8/1988 | O'Rourke et al. | ............. 36/89 |
| 4,811,500 A * | 3/1989 | Maccano | ............. 36/91 |
| 5,209,722 A | 5/1993 | Miklaus et al. | |
| 5,269,078 A | 12/1993 | Cochrane | |
| 5,323,549 A | 6/1994 | Segel et al. | |
| 5,367,792 A | 11/1994 | Richard et al. | |
| 5,408,761 A * | 4/1995 | Gazzano | ............. 36/88 |

(Continued)

FOREIGN PATENT DOCUMENTS

DE    197 02 978 A 1    7/1998

*Primary Examiner*—Ted Kavanaugh
(74) *Attorney, Agent, or Firm*—Sheppard, Mullin, Richter & Hampton LLP

(57) ABSTRACT

A supinator strap integrated with an athletic shoe, sock, or brace for preventing foot and ankle injuries. In the shoe, the supinator strap includes an arch support band that extends from the bottom of the shoe, just under the arch area, around the inner side of the shoe and over the top of the shoe, toward the outer side of the shoe. The supinator strap further includes a rear ankle support band that extends laterally from the arch support band and wraps from the inner side of the shoe, around the rear ankle/heel and toward the outer side of the shoe. In a preferred embodiment, both the foot and rear ankle support band and the arch support band are fully adjustable. The supinator strap provides additional support and stability to the foot and ankle when the shoe is worn, thereby helping to prevent injuries caused by excessive supination or pronation of the foot and ankle. A bridge support helps cushion the foot. An ankle stabilizing strap helps prevent ankle injuries by stabilizing the forefoot, heel, and ankle. In the sock and the brace, the supinator strap operates in a similar manner.

29 Claims, 9 Drawing Sheets

U.S. PATENT DOCUMENTS

| | | | |
|---|---|---|---|
| 5,440,826 A * | 8/1995 | Whatley | 36/25 R |
| 5,445,603 A | 8/1995 | Wilkerson | |
| 5,595,003 A | 1/1997 | Snow | |
| 5,755,679 A | 5/1998 | Selner et al. | 602/27 |
| 5,819,439 A | 10/1998 | Sanchez | |
| 5,822,887 A | 10/1998 | Turner | |
| 6,000,148 A * | 12/1999 | Cretinon | 36/88 |
| 6,041,521 A | 3/2000 | Wong | |
| D423,202 S * | 4/2000 | Lubart | D2/961 |
| 6,237,251 B1 * | 5/2001 | Litchfield et al. | 36/25 R |
| 2002/0088144 A1 | 7/2002 | Katz et al. | |

* cited by examiner

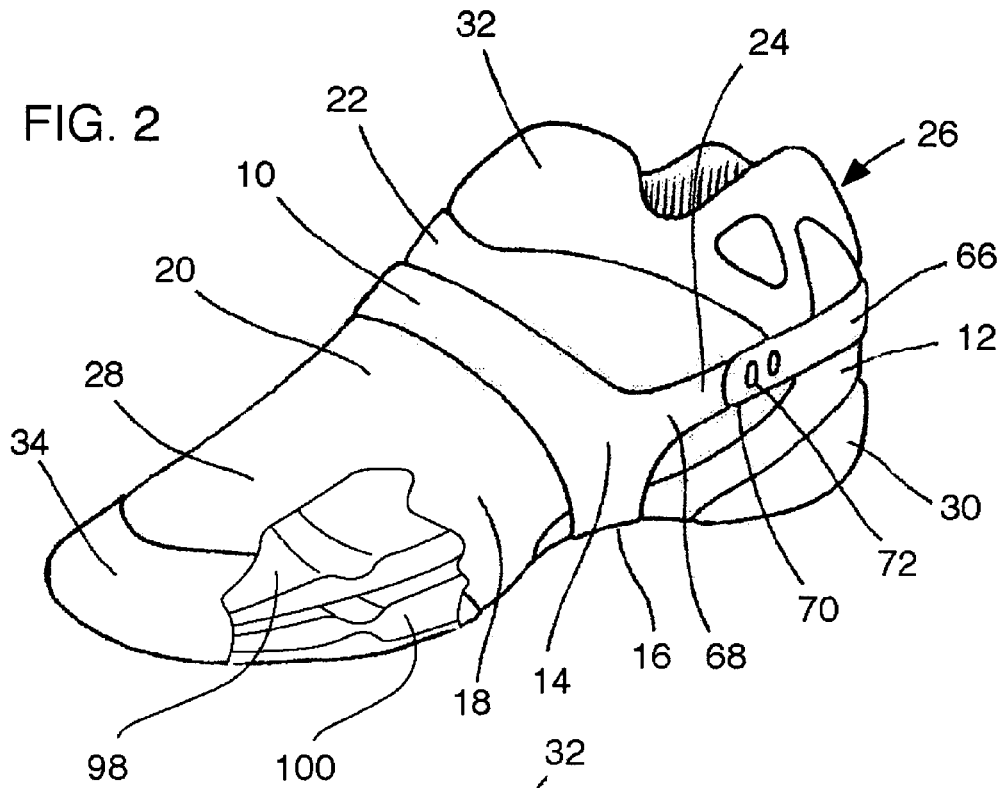

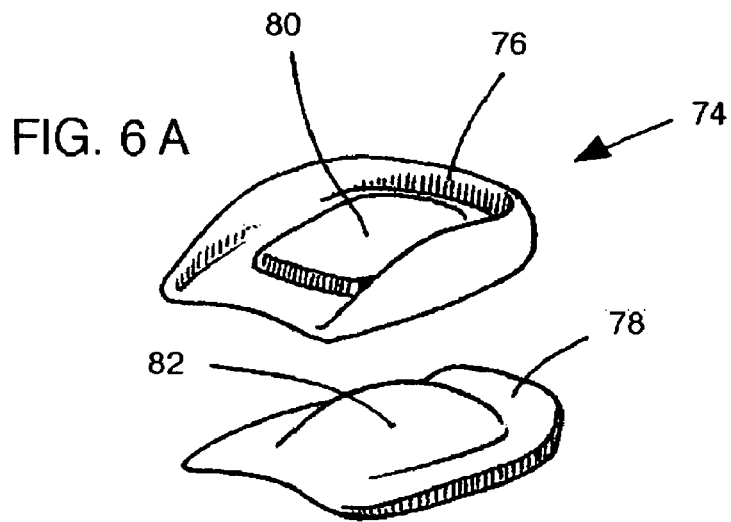
FIG. 6 A
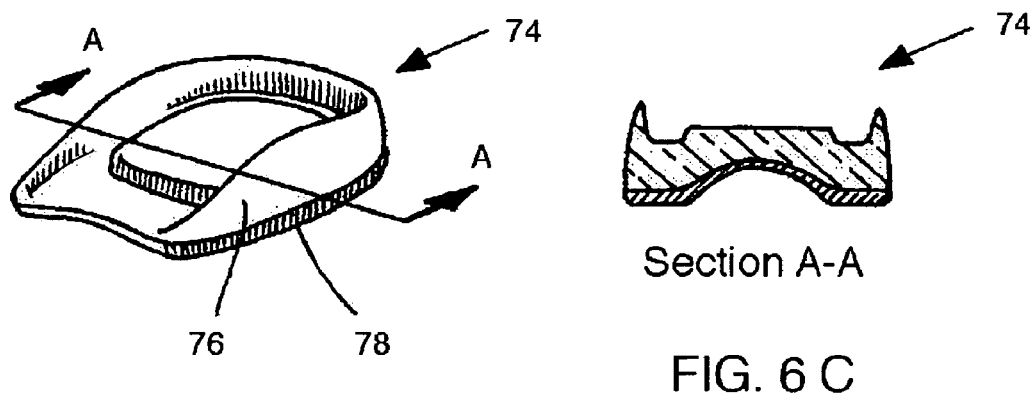
FIG. 6 B
Section A-A
FIG. 6 C

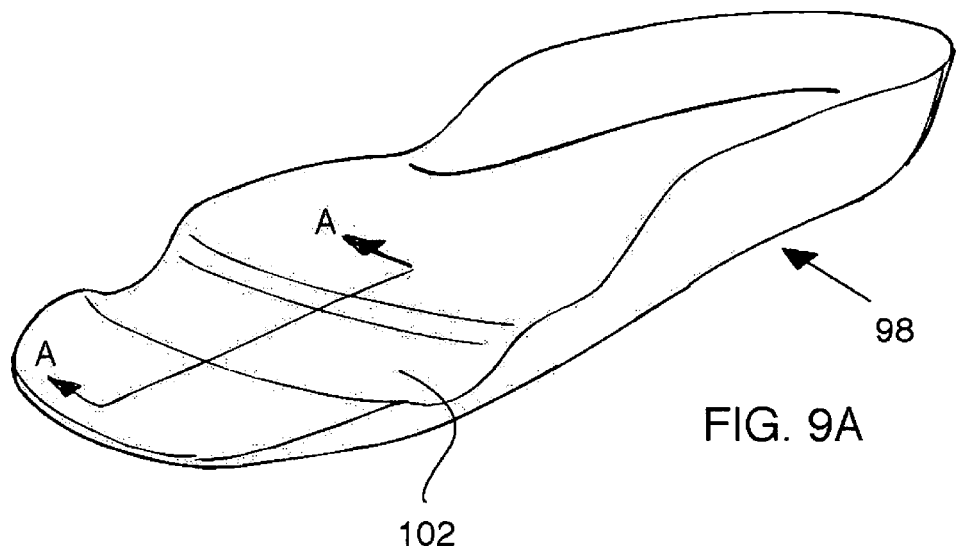
FIG. 9A
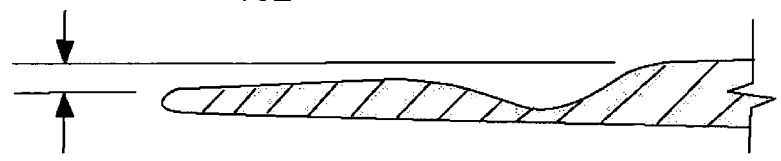
FIG. 9B   Section A-A
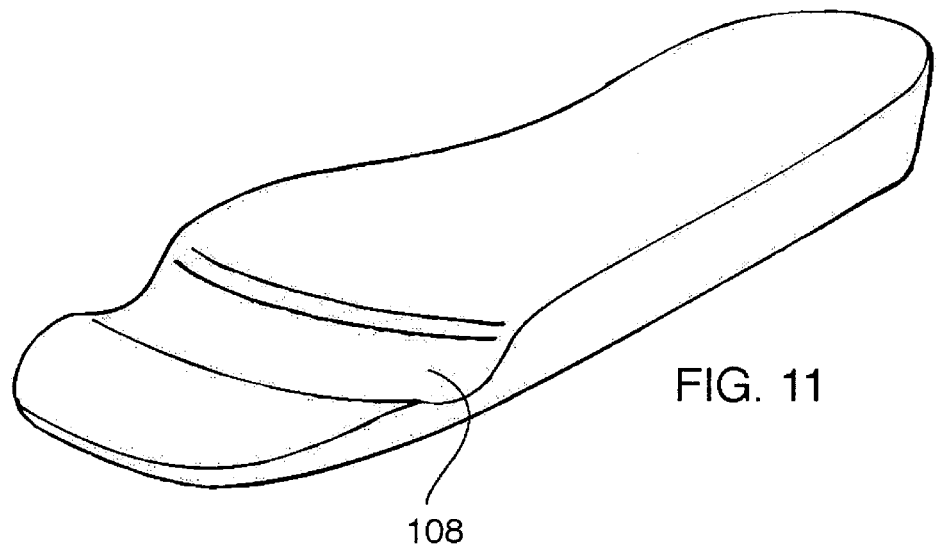
FIG. 11

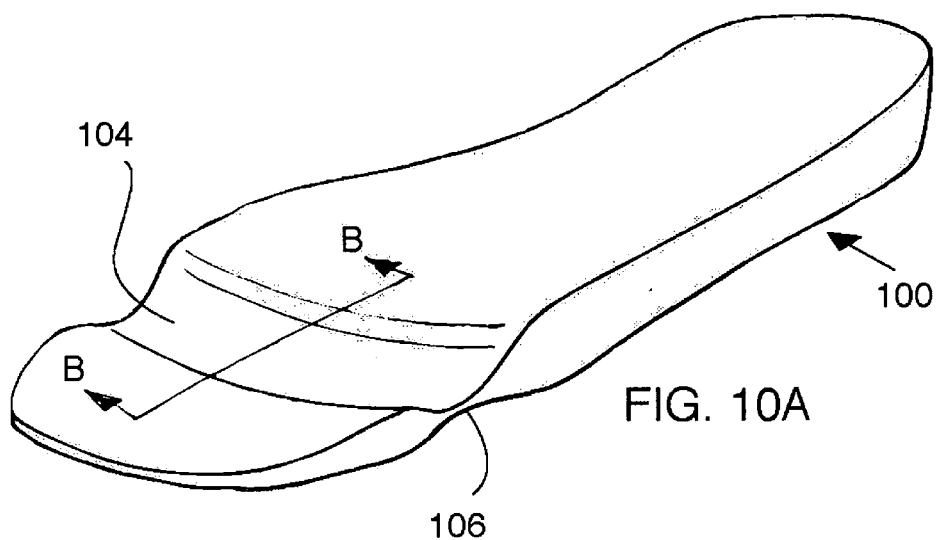
FIG. 10A
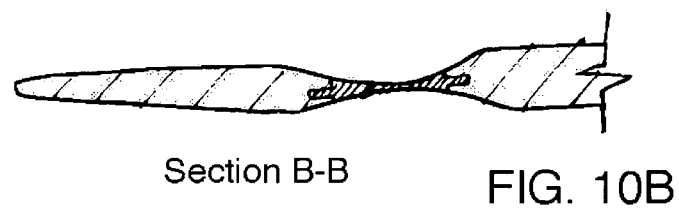
Section B-B FIG. 10B
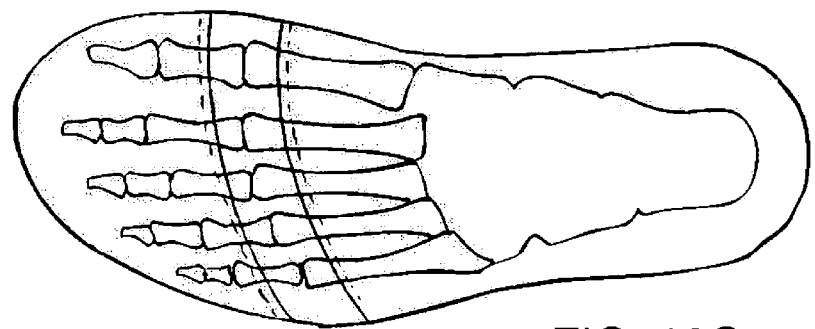
FIG. 10C

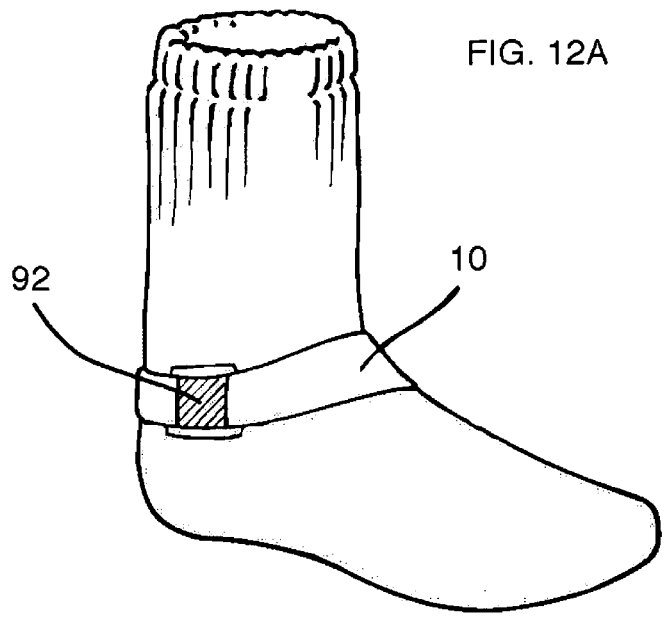
FIG. 12A
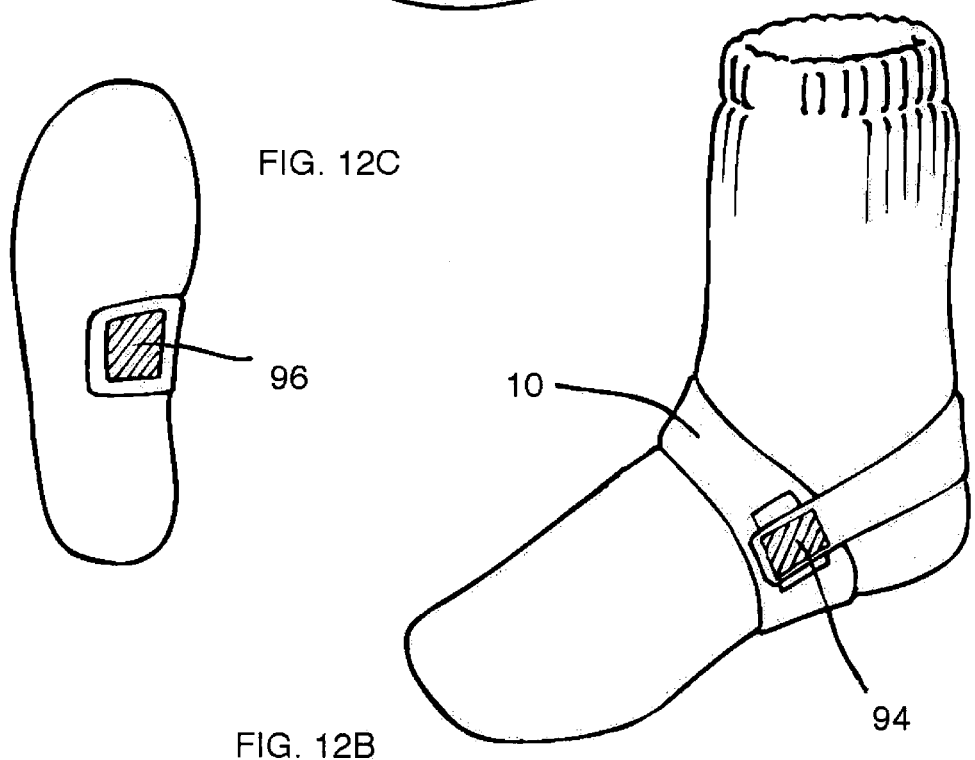
FIG. 12C
FIG. 12B

FIG. 13A
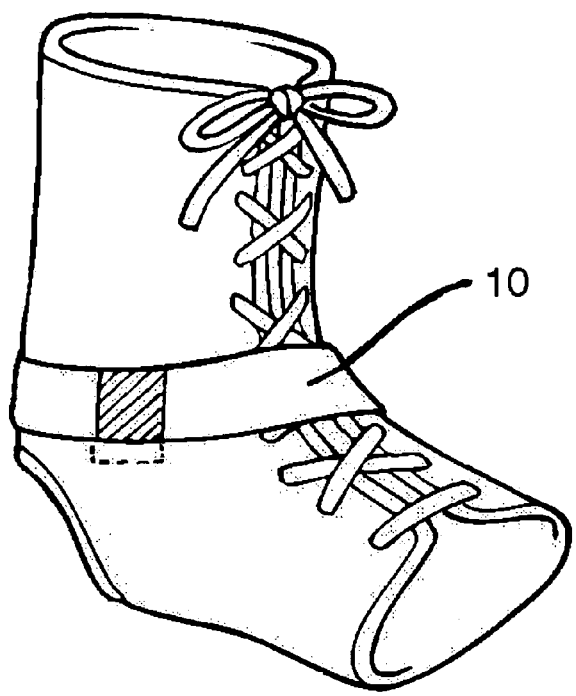
Fig. 13C
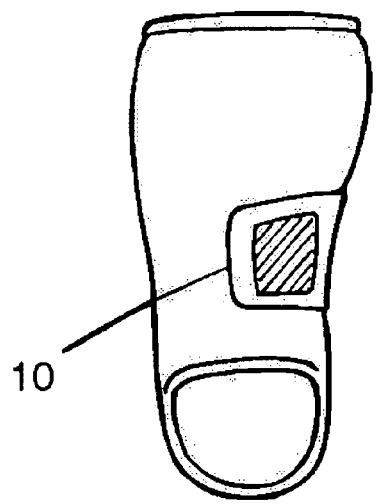
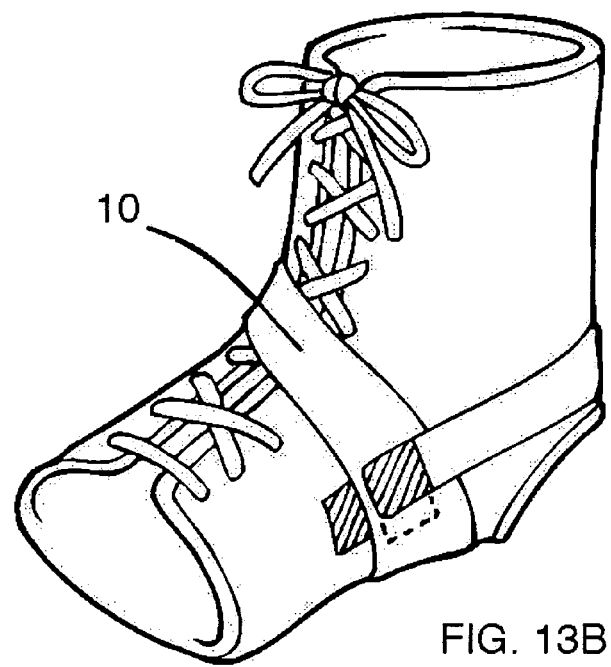
FIG. 13B

ATHLETIC FOOTWEAR AND THE LIKE WITH INTEGRAL SUPINATOR DEVICE

BACKGROUND OF THE INVENTION

The present invention relates to athletic footwear and the like, such as shoes, socks, and braces, with an integral supinator device designed to provide ankle, heel and arch support and to prevent injuries due to excessive supination or pronation.

A normal human gait cycle consists of four phases: a contact phase in which the heel alone makes initial contact with the ground, a mid-stance phase in which the entire sole or plantar surface of the foot is in contact with the ground, a propulsion phase in which the ball of the foot pushes off from the ground, and a swing phase in which the foot and leg swing forward without contacting the ground.

Ordinarily, some pronation (inward rolling) and supination (outward rolling) of the foot during normal walking or running is desirable. Although some pronation and/or supination is desirable, many people are troubled by excessive pronation or supination in which the foot and ankle roll too far inward or outward and the bones of the foot become hyper-mobile relative to one another. Excessive pronation or supination during the gait cycle can result in exaggerated back and forth rotational movement of the leg and knee with accompanying results that are highly undesirable. For example, various forms of muscular fatigue, arch strains to the foot, pains in the knee joint and patella (knee cap), and numerous foot and heel injuries can all be caused by excessive pronation or supination.

Excessive pronation or supination can be a particular problem for athletes. Athletic shoes are often used in high impact activities, such as basketball or soccer, and are normally designed for speed and comfort. While athletic shoes known in the art as having customized and cushioned soles may provide additional comfort and a certain amount of "bounce" or returned energy, these shoes are generally not well designed to prevent foot and ankle injuries.

As a result of its relative anatomical instability and its relative weakness, the ankle joint is frequently injured when wearing athletic shoes and engaging in certain athletic activities. For example, injuries are often caused in basketball or soccer by stepping on another player's foot, landing on a foot at an improper angle, rolling the ankle when maneuvering in a lateral fashion, or slipping while running and twisting the ankle. These injuries often develop from excessive supination or excessive pronation of the foot and ankle.

Ankle and knee injuries caused by excessive supination or excessive pronation are commonly suffered by athletes while wearing conventional athletic shoes because these shoes are not specifically designed to prevent this type of injury. An ankle injury involves the motion of the forefoot, heel, and ankle. To effectively prevent an ankle injury, the forefoot, heel, and ankle must be stabilized together and controlled. Also, for improved performance, torque control is necessary to bring alignment back to center quickly. Torque control of the forefoot, which acts as a lever arm, is also necessary to prevent additional injuries to the ankle. Accordingly, what is needed is a new athletic shoe which provides support to the ankle, heel and arch, designed to prevent foot and ankle injuries caused by excessive supination or pronation.

SUMMARY OF THE INVENTION

The present invention resides in athletic footwear and the like having a built-in supinator strap designed to provide ankle, heel, and arch support and to prevent foot and ankle injuries. The supinator strap is designed to support the foot and prevent excessive pronation of the foot and ankle by realigning the foot in a supinatory direction. In an alternative embodiments, the supinator strap may be integrated with an athletic shoe, an athletic sock, or an athletic brace.

In the presently preferred athletic shoe embodiment of the invention, the supinator strap may include an arch support band which extends from the bottom of the shoe, under the arch of the foot, and over the bridge or top of the shoe. The supinator strap further may include a rear ankle support band which wraps from the arch on a first side of the shoe and around the rear heel and ankle. In concert, these two support bands act together to provide arch, heel and ankle support to the foot when the shoe is worn, thereby helping to align the foot in a supinatory direction and prevent injuries due to excessive pronation of the foot and ankle. The arch support band and the rear ankle support band each may be formed of a resilient and sturdy elastomer, and they each may be individually adjustable to vary the tension on the strap.

The athletic shoe of the first embodiment of the invention also may include a reinforced heel stabilizing and forefoot torque control member designed to provide additional support and prevent excessive supination and pronation of the foot and ankle. The heel stabilizing and forefoot torque control member may extend from the heel to the forefoot just behind the ball of the foot to allow bending of the foot during propulsion. The heel stabilizing and forefoot torque control member also may extend around the sides of the foot, and up around the heel at the back end of the shoe. The heel stabilizing and forefoot torque control member may be formed by injection-molding of durable plastic.

The heel stabilizing and forefoot torque control member may include an ankle stabilizing strap which wraps around the ankle bones (malleolus), extending around the front of the ankle from one side of the shoe to the opposite side. Preferably, the ankle stabilizing strap is removably coupled on one side of the heel stabilizing and forefoot torque control member via a quick release fastener or mechanism such that the ankle stabilizing strap can be readily opened and closed. When opened, the ankle stabilizing strap allows the foot to be placed into the shoe. Once the shoe is on the foot, the ankle stabilizing strap may be closed to secure the heel stabilizing and forefoot torque control member around the heel and ankle. This combination stabilizes the ankle in an effective manner.

The ankle stabilizing strap includes an opening or cavity through or into which the lateral malleolus or prominent ankle bone can protrude for comfort. The ankle stabilizing strap keeps the heel stabilizing and forefoot torque control member close to the ankle on both sides, thereby preventing the heel stabilizing and forefoot torque control member from pulling away from the ankle when the shoe is worn and providing additional support to the foot and ankle in order to prevent excessive supination and pronation.

The athletic shoe of the first embodiment of the present invention further may include a rear foot cushioning system which provides cushioning and stabilization at the heel. This rear foot cushioning system includes a multi-level heel comprised of an external heel cushion and a cantilever-like molded outsole. Preferably, the rear cushioning system further may include a bridge support for adding further stability and shock absorption at the heel of the shoe.

The athletic shoe of the first embodiment of the present invention further may include a forefoot cushioning system which provides cushioning and stabilization at the metatarsal head of the foot, which is also known as the ball of the foot. This forefoot cushioning system includes a single cantilever-like molded insole and a double cantilever-like molded midsole. This allows a substantial reduction of pressure at the ball of the foot.

The athletic sock embodiment of the invention includes a supinator strap with an arch support band and rear ankle support band integral with the sock. The supinator strap of the athletic sock embodiment operates in a similar manner as the athletic shoe embodiment.

The athletic brace embodiment of the invention includes a supinator strap with an arch support band and rear ankle support band integral with the brace. The supinator strap of the athletic brace operates in a similar manner as the supinator strap in the athletic shoe and sock embodiments.

Other features and advantages of the invention will become apparent from the following detailed description of the preferred embodiment, taken in conjunction with the accompanying drawings, which illustrate, by way of example, the principles of the invention.

BRIEF DESCRIPTION OF THE DRAWINGS

The invention will now be described in detail with reference to the presently preferred embodiments shown in the drawings, which are provided only as an example to illustrate the principles of the invention. The invention is not limited to the embodiments shown, and variations within the scope of the invention will be apparent to those skilled in the art. The embodiments are not shown or described in more detail than necessary to describe the invention, and the manner and process of making and using it, to those skilled in the art.

In the drawings:

FIG. 2 is a medial view of the right foot of an athletic shoe with a built-in supinator strap in accordance with a preferred embodiment of the present invention, with a cut-away showing the interior of the shoe;

FIG. 3 is a lateral view of the right foot of an athletic shoe with the built-in supinator strap of FIG. 2;

FIGS. 6A and 6B are perspective views illustrating a rear heel cushioning system in accordance with a preferred embodiment of the present invention;

FIG. 6C is a cross-sectional view of the rear heel cushioning system taken along the line A—A in FIG. 6B.

FIG. 9A is a lateral view of the single cantilever-like molded insole of the forefoot cushioning system;

FIG. 9B is a cross-section of FIG. 9A through A—A;

FIG. 10A is a lateral view of the double cantilever-like molded midsole of the forefoot cushioning system;

FIG. 10B is a cross-section of FIG. 10A through B—B;

FIG. 10C is a top view of the midsole of FIG. 10A illustrating the approximate location of a human foot in relation to the midsole;

FIG. 11 is a lateral view of the alternative embodiment single cantilever-like molded midsole of the forefoot cushioning system;

FIG. 12A is a medial view of the right foot of an athletic sock with a supinator strap, in accordance with an alternate embodiment of the present invention;

FIG. 12B is a lateral view of the right foot of an athletic sock with the supinator strap of FIG. 12A;

FIG. 12C is a bottom view of the right foot of an athletic sock with the supinator strap of FIG. 9A;

FIG. 13A is a medial view of the right foot of an athletic brace with a supinator strap in accordance with an alternate embodiment of the present invention;

FIG. 13B is a lateral view of the right foot of an athletic brace with the supinator strap of FIG. 13A;

FIG. 13C is a bottom view of the right foot of an athletic brace with the supinator strap of FIG. 13A;

DETAILED DESCRIPTION OF PREFERRED EMBODIMENTS

Figure 1:
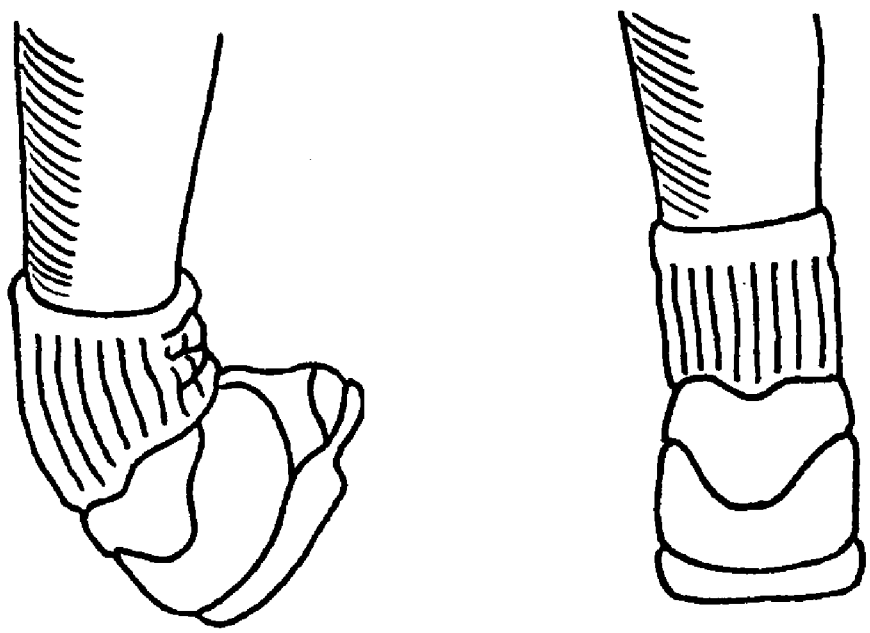
FIG. 1A is an illustration of the concept of inversion sprain or supination with a typical athletic shoe.
FIG. 1B is an illustration of the concept of an eversion sprain or pronation with a typical athletic shoe.
Figure 1:
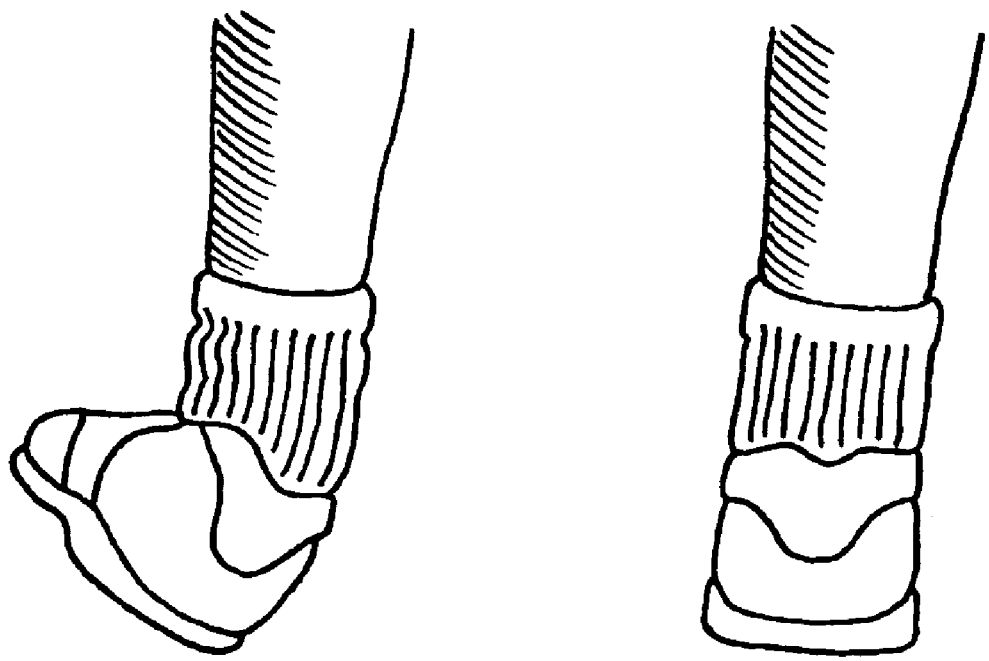

Referring now to the drawings, and particularly to FIGS. 1A and 1B thereof, there are shown illustrations of the types of ankle injuries the present invention is intended to prevent. These include an inversion sprain, which occurs when there is excessive supination of the foot and ankle (FIG. 1A), and an eversion sprain, which occurs when there is excessive pronation of the foot and ankle (FIG. 1B). In an inversion sprain the foot and ankle roll outward on the frontal plane, and the forefoot adducts or twists inward relative to the rearfoot on the traverse plane. This adduction increases the lever arm because the forefoot is far away from the axis of the ankle and adds to the severity of injury. In an eversion sprain the foot and ankle roll inward on the frontal plane, and the forefoot abducts or twists outward relative to the rearfoot on the traverse plane. These injuries can be very serious and can lead to additional injuries involving other areas, including the knee. The invention is embodied in an athletic shoe and is designed to prevent excessive supination or pronation.

Referring to FIG. 2 there is shown a medial view of the invention embodied in the right foot of a built-in supinator strap 10 integral with an athletic shoe and ankle and heel stabilizing and forefoot torque control member 12 for preventing foot and ankle injuries in accordance with the present invention. Even though the drawing is of a right foot of the shoe, it should be understood that the mirror image of the invention embodied in the right foot of the shoe would apply to the left foot of the shoe. The supinator strap 10 and ankle and heel stabilizing and forefoot torque control member 12 work together, in concert, to prevent excessive pronation or excessive supination of the foot and ankle.

In a preferred embodiment, the supinator strap 10 includes an arch support band 14 that extends from the bottom of the inner side of the interior of the shoe 16, just under the arch area of the foot, through the fabric of the shoe around the inner side of the shoe within the fabric of the shoe and over bridge or top of the shoe through the fabric of the shoe to the exterior of the shoe, toward the outer side of the exterior of the shoe 22. The supinator strap 10 further includes a foot and rear ankle support band 24 that extends from the arch support band 14 around the arch area on the inner side of the shoe within the fabric of the shoe. The foot and rear ankle support band 24 wraps from the arch area on the inner side of the shoe within the fabric of the shoe, around the rear heel of the shoe toward the outer side of the shoe through the fabric of the shoe to the exterior of the shoe, and is attached at the rear heel 26. The band may be attached using of many common mechanisms, including a quick-release and velcro. Alternatively, the band can be located on the exterior of the shoe rather than located within the fabric. In a preferred embodiment, the supinator strap 10 is made from a durable elastomer, such as polyurethane, and both the foot and rear ankle support band 24 and the arch support band 14 are fully adjustable. The supinator strap 10 provides support and stability to the foot and ankle when the shoe is worn, thereby helping to prevent injuries caused by excessive pronation of the foot and ankle. The supinator strap 10 acts to also lift and support the arch of the foot. It reduces pronation and assists with supination.

FIGS. 2 and 3 show inner and outer side views of the right foot of an athletic shoe with built-in supinator strap 10 in accordance with a preferred embodiment of the present invention. Even though the drawing is of a right foot of the shoe, it should be understood that the mirror image of the invention embodied in the right foot of the shoe would apply to the left foot of the shoe. Referring to FIG. 2, an athletic shoe of the present invention includes a main shoe body 28 formed on a rubber composite outsole (not shown) and rear heel cushioning system 30, thereby forming a shoe cavity for accommodating a human foot when the shoe is worn. The main shoe body 28 can be attached to the outsole by glue and/or stitching, for example. The main shoe body 28 is preferably formed of a lightweight, comfortable and durable material such as nylon, nylon mesh, leather, synthetic leather, or the like. The rubber composite outsole (not shown) extends along the bottom of the exterior of the shoe from the toe to the area where the arch and heel meet.

Preferably, the shoe further includes a plastic injection-molded reinforced ankle and heel stabilizing and forefoot torque control member 12 that extends along the bottom of the interior of the shoe from just above the rear heel cushioning system 30 toward the middle of the shoe to the area just behind the ball of the foot. The reinforced ankle and heel stabilizing and forefoot torque control member 12 is coupled to the shoe by gluing, stitching, riveting, or any other mechanism for coupling. The ankle and heel stabilizing and forefoot torque control member 12 curves upward at the back of the shoe from the heel and toward and around the ankle portion of the shoe, thereby providing additional support and stability to the heel and ankle. The ankle and heel stabilizing and forefoot torque control member 12 is preferably comprised of durable plastic and provides additional support and stability to the arch and ankles in order to prevent excessive supination when the shoe is worn.

In a preferred embodiment, the ankle and heel stabilizing and forefoot torque control member 12 includes an ankle stabilizing strap 32 which wraps around the ankle bone (the malleolus), extending around the front of the ankle from one side of the exterior of the shoe to the opposite side. The ankle stabilizing strap 32 can be made of a semi-flexible material, for example. Preferably, the ankle stabilizing strap 32 is removably coupled on one side of the ankle and heel stabilizing and forefoot torque control member 12 via a quick release such that the ankle stabilizing strap 32 can be opened and/or closed. The quick release can be a push button, release tension, strap, or other mechanism. The ankle stabilizing strap 32 can be made from a semi-rigid material, such as synthetic leather or a comparable material. The ankle stabilizing strap 32 is opened to allow the foot to placed into the shoe. Once the shoe is placed on the foot, the ankle stabilizing strap 32 is preferably closed, thereby securing the ankle and heel stabilizing and forefoot torque control member 12 around the heel and ankle. The ankle and heel stabilizing and forefoot torque control member 12 is described in greater detail further hereinafter. The supinator strap 10 also secures the foot and ankle into the shoe. This allows the shoe to be closed without the need for laces or a similar tightening mechanism. However, laces or zippers can be added to the shoe.

As further illustrated in FIG. 2, a front end of the main shoe body 28 is supplemented by a toe-protection member 34, which covers the toe area of the shoe. In a preferred embodiment, the toe-protection member 34 is comprised of a sturdy, reinforced, natural or synthetic rubber material in order to provide additional support and protection of the toes when the shoe is worn. The toe-protection member 34 can be coupled to the shoe by gluing, stitching, or mechanical fastening, for example.

FIG. 2 illustrated a built-in supinator strap 10 integral with an athletic shoe of the present invention. The built-in supinator strap 10 which is preferably made from a durable elastomer, such as polyurethane or vinyl. The supinator strap 10 preferably originates from the bottom of the inner side of the interior of the shoe (not shown), through the fabric of the shoe within the fabric, near the arch area of the foot. Preferably, the supinator strap 10 extends around the shoe in two different directions. In a first direction, the supinator strap 10 includes an arch support band 14 which extends from the bottom of the inner side of the interior of the shoe (not shown), in an around the arch area through the fabric of the shoe within the fabric, and around a first inner side of the shoe out of the fabric of the shoe to the exterior. From the first inner side of the shoe, the adjustable arch support band 14 extends over the bridge or top of the shoe, toward the outer side of the shoe. In a second direction, the supinator strap 10 includes a foot and rear ankle support band 24 which extends from the arch support band 14 and wraps from the first inner side of the exterior of the shoe 18 around the rear ankle/heel of the exterior of the shoe 26.

Preferably, both the arch support band 14 and the foot and rear ankle support band 24 are fully adjustable, as described further hereinafter. In concert, they provide additional support and stability to the foot and ankle when the shoe is worn, thereby reducing stress on the ankle and preventing excessive pronation of the foot and ankle. Because the foot and ankle are connected at the heel bone and the talus, any reduction of stress in the foot also directly reduces stress to the ankle joint, ligaments, tendons and muscles of the ankle, leg and knee.

Referring now to FIG. 3, there is shown an outer side or lateral view of the right of an athletic shoe of the present invention which illustrates the main shoe body 28 and other features of the invention visible on the outer side of the shoe. As further illustrated in FIG. 3, an arch support band 14 of the supinator strap 10 extends over the bridge or top of the shoe and toward the outer side of the shoe, where the arch support band 14 preferably splits into a "Y" shaped configuration on the outer side of the shoe. FIG. 3 also shows the foot and rear ankle support band 24 extending around the rear heel of the exterior of the shoe 26.

In a preferred embodiment, a loop 36 is positioned at the bridge or top of the exterior of the shoe 20. The loop may be sewn or glued to the shoe. This loop 36 is preferably formed of plastic or nylon material and is designed to prevent the supinator strap 10 from sliding down the front of the exterior of the shoe when the shoe is worn. As further illustrated in FIG. 3, the arch support band 14 of the supinator strap 10 passes through the loop 36 located at the bridge or top of the exterior of the shoe 20, as the arch support band 14 extends over the bridge or top of the exterior of the shoe 20 and toward the outer side of the exterior of the shoe 22.

Figure 4:
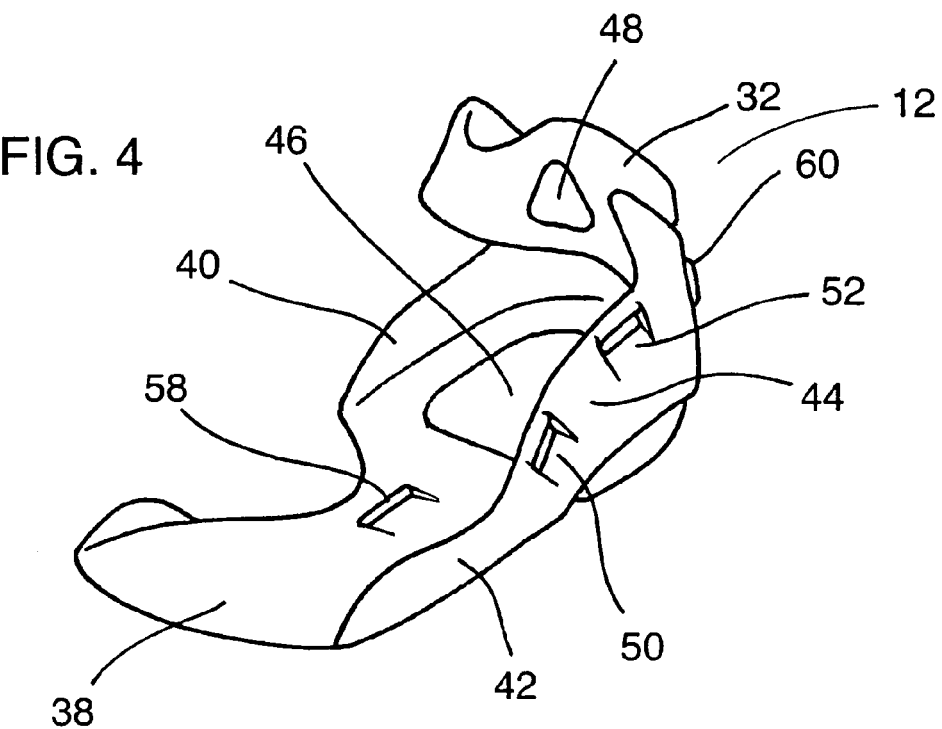
FIG. 4 is a perspective view of a heel stabilizing and forefoot torque control member including an ankle stabilizing strap in accordance with a preferred embodiment of the present invention.

FIG. 4 illustrates a perspective view of just the ankle and heel stabilizing and forefoot torque control member 12 in accordance with a preferred embodiment of the present invention. The ankle and heel stabilizing and forefoot torque control member 12 is preferably comprised of durable plastic and provides additional stability to the arch and ankles when the shoe is worn. The ankle and heel stabilizing and forefoot torque control member 12 includes a base 38, opposing inner and outer side walls 40 and 42, and a curved upward back wall 44, which cradle the foot when the shoe is worn and provide arch and ankle support to the foot. The ankle and heel stabilizing and forefoot torque control member 12 preferably includes an aperture 46 located in its base 38 near the heel. Preferably, the rear heel cushioning system 30 will partially extend through this aperture 46 and provide comfort and shock absorption at the heel, as further described hereinafter. It is understood that in a preferred embodiment, the ankle and heel stabilizing and forefoot torque control member 12 is actually integral to the shoe such that is placed in the interior of the shoe and yet extends to the exterior of the shoe, as shown in FIGS. 2 and 3.

The ankle stabilizing strap 32 is preferably made out of a semi-rigid material, such as a stiff natural or synthetic leather or a similar material and it preferably includes a cavity 48 which allows the lateral malleolus or prominent ankle bone to protrude through the ankle stabilizing strap 32 for comfort. Additional padding may be provided within the ankle stabilizing strap 32 in and around the cavity 48 in order to provide additional comfort to the ankle bone when the shoe is worn. The ankle stabilizing strap 32 keeps the ankle and heel stabilizing and forefoot torque control member 12 close to the ankle on both sides, thereby preventing the ankle and heel stabilizing and forefoot torque control member 12 from pulling away from the ankle when the shoe is worn and providing additional support to the foot and ankle in order to prevent excessive supination.

Figure 5:
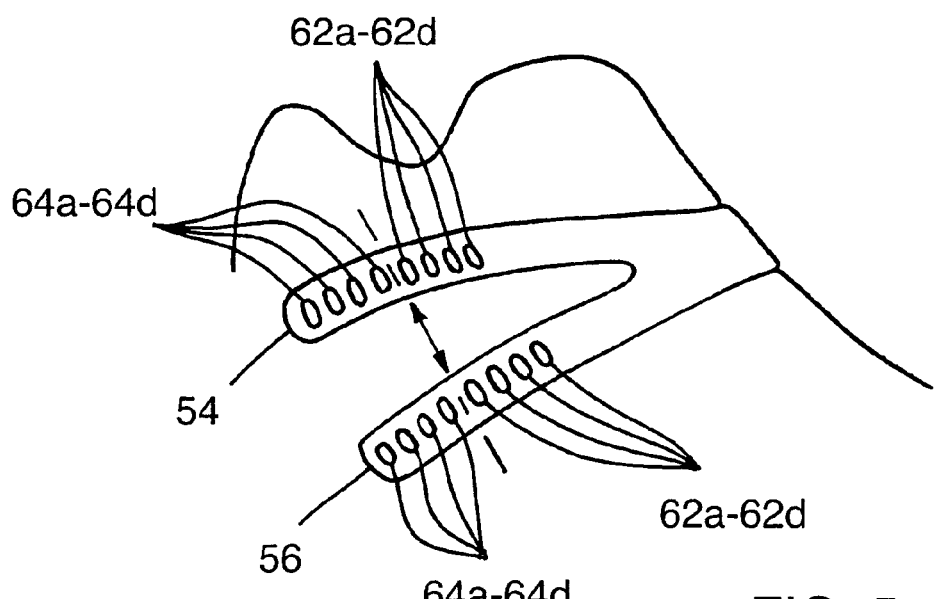
FIG. 5 is a perspective view illustrating the "Y" shaped configuration of an adjustable arch support band of a supinator strap in accordance with a preferred embodiment of the present invention.

As further shown in FIG. 4, the ankle and heel stabilizing and forefoot torque control member 12 preferably includes two fastening slots 50 and 52 located on the outer side wall 42 of the ankle and heel stabilizing and forefoot torque control member 12. Preferably, these fastening slots 50 and 52 are positioned on outer side wall 42 such that they will be exposed on the outer side of the exterior of the shoe. The ankle and heel stabilizing and forefoot torque control member 12 shown in FIG. 4 is for use on a shoe designed for the left foot. Even though the drawing is of a left foot of the member, it should be understood that the mirror image of the invention embodied in the left foot of the member would apply to the right foot of the member. Each of the ends 54 and 56 in the "Y" shaped configuration, as shown in FIG. 5, of the adjustable arch support band 14 of the supinator strap 10 extends through one of these respective fastening slots 50 and 52 and folds over onto itself for secure fastening, as further described hereinafter, and may also provide for quick-release fastening.

The ankle and heel stabilizing and forefoot torque control member 12 further includes two origination clasps 58 and 60, which are coupled to the shoe via glue, pressure, or other methods. The clasps can be made of plastic, velcro, metal, or other material. A first origination clasp 58 is positioned along the base 38 of the ankle and heel stabilizing and forefoot torque control member 12 near the arch area. This first origination clasp 58 is where the arch support band 14 of the supinator strap 10 originates. As described earlier, the arch support band 14 extends from the bottom of the inner side of the shoe, across the arch area, and around a first inner side of the shoe. A second origination clasp 60 is positioned on the back wall 44 of the ankle and heel stabilizing and forefoot torque control member 12 near the heel/ankle area. This second origination clasp 60 is where the foot and rear ankle support band 24 originates, as described in greater detail further hereinafter. The clasps may be molded onto the ankle and heel stabilizing and forefoot torque control member 12.

As described earlier, the arch support band 14 of the supinator strap 10 is preferably fully adjustable. FIG. 5 illustrates a perspective view of the "Y" shaped configuration of the adjustable arch support band 14 of the supinator strap 10. As shown in FIG. 5, in a preferred embodiment of the athletic shoe the arch support band 14 is configured with hooks or fastening buttons 62a through 62d on each of the ends 54 and 56 of the "Y" shape. The ends 54 and 56 of the "Y" shape are also further configured with holes or button snaps 64a through 64d for accommodating the hooks or fastening buttons 62a through 62d. As illustrated in FIG. 3B, each of the ends 54 and 56 of the "Y" shaped configuration of the adjustable arch support band 14 of the supinator strap 10 extends through one of the respective fastening slots 50 and 52 in the ankle and heel stabilizing and forefoot torque control member 12, folds over onto itself, and is securely fastened into place via the hooks or fastening buttons 62a through 62d and the holes or button snaps 64a through 64d located on the "Y" shaped ends 54 and 56.

As explained earlier, the supinator strap 10 is made of a durable elastomer such as polyurethane, in this way the adjustable arch support band 14 of the supinator strap 10 is pulled tightly over the bridge or top of the exterior of the shoe 20 and the "Y" ends 54 and 56 are passed through the two fastening slots 50 and 52 of the ankle and heel stabilizing and forefoot torque control member 12 and securely coupled in order to provide a firm and stable support to both the arch and front of the ankle. The arch support band 14 is fully adjustable such that any hook or fastening button 62a through 62d may be mated with any hole or button snap 64a through 64d as the arch support band 14 is stretched, in order to provide firm yet comfortable support.

As also described earlier, as shown in FIG. 2, the foot and rear ankle support band 24 of the supinator strap 10 is preferably fully adjustable. Accordingly, in a preferred embodiment of the athletic shoe, the foot and rear ankle support band 24 is actually comprised of two pieces, a first piece 66 and a second piece 68. A first piece 66 is coupled to the second origination clasp 60 located on the back wall 44 of the ankle and heel stabilizing and forefoot torque control member 12 at the rear ankle/heel of the exterior of the shoe 26. The clasps may be molded onto the ankle and heel stabilizing and forefoot torque control member 12. This first piece 66 extends from the rear ankle/heel of the exterior of the shoe 26 to the inner side of the exterior of the shoe 18. Preferably, this first piece 66 of the foot and rear ankle support band 24 is configured with holes or button snaps 70. Alternatively; the first piece 66 can be configured with velcro, snaps, quick-release mechanisms, buttons, clasps, or hooks, for example.

A second piece 68 of the foot and rear ankle support band 24 extends laterally from the arch support band 14 from the inner side of the exterior of the shoe 18 and toward rear ankle/heel of the exterior of the shoe 26. Preferably, this second piece 68 is further configured with hooks or fastening buttons 72. Preferably, the first and second pieces 66 and 68 are pulled together from opposite directions and securely coupled using the hooks or fastening buttons 72 and the holes or button snaps 70. In this way the foot and rear ankle support band 24 of the supinator strap 10 is pulled tightly from the inner side of the exterior of the shoe 18 and from the rear ankle/heel of the exterior of the shoe 26, and securely coupled in order to provide a firm and stable support to the foot, heel, and ankle when the shoe is worn.

The arch support band 14 and the foot and rear ankle support band 24 work together to provide support and prevent excessive pronation of the foot and ankle. The arch support band 14 keeps the medial arch of the foot from rolling inward, pulls the arch upward, and prevents the ankle from sliding forward in the shoe. The foot and rear ankle support band 24 keeps the arch and foot from falling and works in the same fashion as the plantar fascia (a ligament in the foot, which is like a band, that serves a similar function). The foot and rear ankle support band 24 acts to provide a tie to the ends of the arch of the foot, which cause the arch to maintain its shape and not fall by preventing the arch from flattening or lengthening. The arch support band 14 and the foot and rear ankle support band 24 work together to support the foot and limit excessive pronation of the foot and ankle.

During normal athletic activity involving running, jumping or walking, more force is normally applied to the heel of a foot. Accordingly, in a preferred embodiment of the present invention, the heel of the athletic shoe includes a rear heel cushioning system 30 specifically designed to receive this additional force and provide a firm, stable, yet comfortable anchor at the heel.

FIGS. 6A–6C illustrate the composite portions of the rear heel cushioning system 30, in accordance with a preferred embodiment of the present invention. As shown, the rear heel cushioning system 30 includes a multi-level heel 74 comprised of an external heel cushion 76 and a cantilever-designed molded outsole 78. In a preferred embodiment, the external heel cushion 76 is formed of polyurethane and the cantilever-designed molded outsole 78 is formed from a resilient, durable rubber. Alternatively, the outsole 78 can also be formed from sponge, foam, plastics, or other materials. The external heel cushion 76 and the cantilever-designed molded outsole 78 are stacked, the former on top of the latter, thereby forming the multi-level heel 74 of the shoe. The external heel cushion 76 and the cantilever-designed molded outsole 78 can be attached by glue, for example.

In a preferred embodiment, both the external heel cushion 76 and the cantilever-designed molded outsole 78 have centrally located caverns 80 and 82, respectively, thereby forming a hollow cavity 84 at the center of the multi-level heel 74 and a convex dome-shape or plateau at the top of the multi-level heel 74. In a preferred embodiment, this elevated dome or plateau will extend through the aperture 46 located in the base 38 near the heel of the ankle and heel stabilizing and forefoot torque control member 12, thereby providing a cushioned shock absorbing system at the heel on the interior of the shoe for comfort and stability.

It is understood that the shape of the multi-level heel 74 is such that it is generally hollow at the center. This is done primarily for comfort, such that when the wearer runs or jumps, the multi-level heel 74 provides sufficient support but does not present a completely hard, firm surface against the heel and arch of the foot. In a preferred embodiment, the rear heel cushioning system 30 has sufficient stability to provide firm arch and heel support to the foot, while acting as a shock absorber whenever the shoe is worn. More particularly, the heels takes the vertical forces applied from the foot when running and/or jumping and spreads them out horizontally over the heel. However, over time, the rear heel cushioning system 30 may lose some of its sturdiness and stability. Under these conditions, the shock absorbing features of the multi-level heel 74 may decrease and it may provide less and less arch and heel support to the foot. In order to prevent this from occurring, the athletic shoe of the present invention is preferably configured with a bridge support 86 in order to help maintain the sturdiness of the heel and prevent the cantilever-designed molded outsole 78 from over-expanding, lengthening, or flattening.

Figure 7:
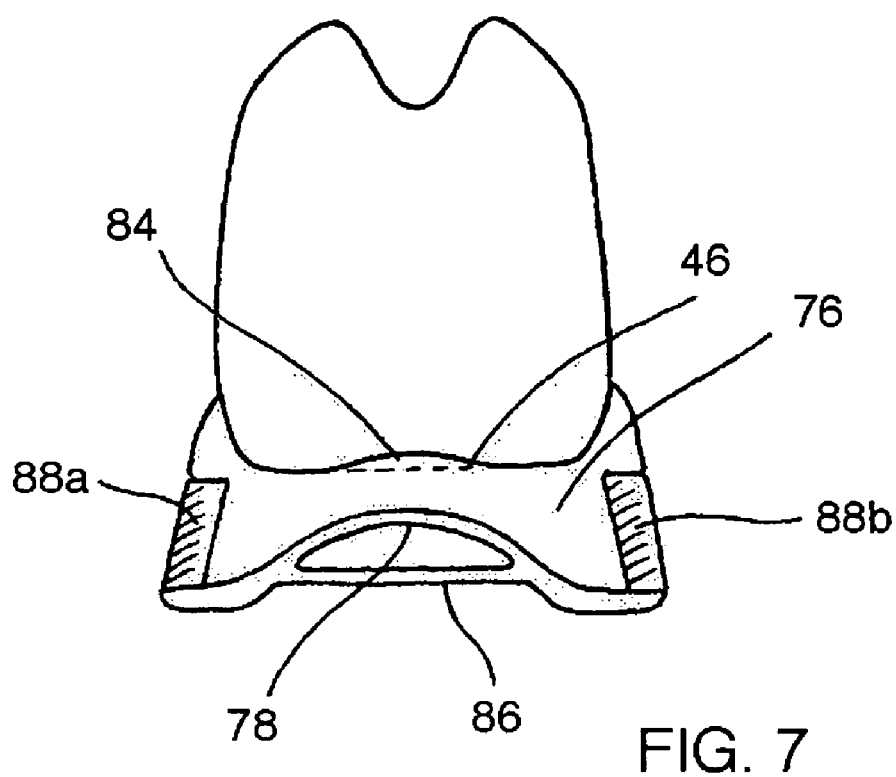
FIG. 7 is a cross-sectional view of an integrated sole bridge support with springs of an alternative embodiment.

FIG. 7 illustrates a cross-sectional view of the athletic shoe from the heel. As shown, the rear heel cushioning system 30 includes the multi-level heel 74 which is comprised of the external heel cushion 76 and the cantilever-designed molded outsole 78. As further explained earlier herein, both the external heel cushion 76 and the cantilever-designed molded outsole 78 have centrally-located elevated caverns 80 and 82, thereby forming a dome-shaped hollow cavity 84 at the center of the multi-level heel 74 and a convex dome-shape or plateau at the top of the multi-level heel 74. It is understood that the hollow cavity 84 may have any alternate shape and the dome-shape is merely illustrative and not intended to be limiting. The dotted line in FIG. 7 illustrates the aperture 46 in the ankle and heel stabilizing and forefoot torque control member 12, through which the multi-level heel 74 preferably extends.

As further illustrated in FIG. 7, the external heel cushion 76 and the cantilever-designed molded outsole 78 are stacked, the former on top of the latter, such that when downward pressure is exerted at the heel area from the foot, the shoe will normally provide some give and the dome-shaped hollow cavity 84 deforms as the shoe is compressed at the heel, thereby converting vertical forces into horizontal forces which are spread across the width of the hollowed heel. Over time, the amount of give and compression might increase, providing less and less shock absorption and cushioning at the heel. However, the athletic shoe of the present invention is preferably equipped with a bridge support 86 which prevents this from occurring.

The bridge support 86 is coupled to the opposite sides of the dome-shaped hollow cavity 84, traversing the entire span of the dome-shaped hollow cavity 84. The bridge support 86 is preferably comprised of a natural or synthetic rubber material having lower elasticity than the rest of the individual components in the multi-level heel 74, such that it holds the dome-shaped hollow cavity 84 together from opposite sides and limits the amount of horizontal spread of the multi-level heel 74 when downward pressure is exerted at the heel of the foot. Furthermore, the bridge support 86 promotes durability by quickly returning the heel to its original state. The bridge support 86 also reduces the fatigue factor on the materials in the multi-level heel 74 so they will not break down as quickly over time. In a preferred embodiment, the multi-level heel 74 with bridge support 86 is designed to absorb impacts as high as seven times (7×) body weight when jumping and three times (3×) body weight during running activity.

Finally, as a further shock absorbing feature, an alternative embodiment of the athletic shoe of the present invention is configured with additional spring supports 88a and 88b located on opposite sides of the multi-level heel 74 and designed to provide further flexibility and a returned energy when the shoe is worn while running or jumping. In this embodiment, the rear heel cushioning system 30 is equipped with two spring supports 88a and 88b, one located on the inner side of the shoe and one located on the outer side of the shoe. The spring supports 88a and 88b can be attached to the shoe by slots, gluing, clasps, bonding, screws, nuts and bolts, and rivets, for example.

Figure 8:
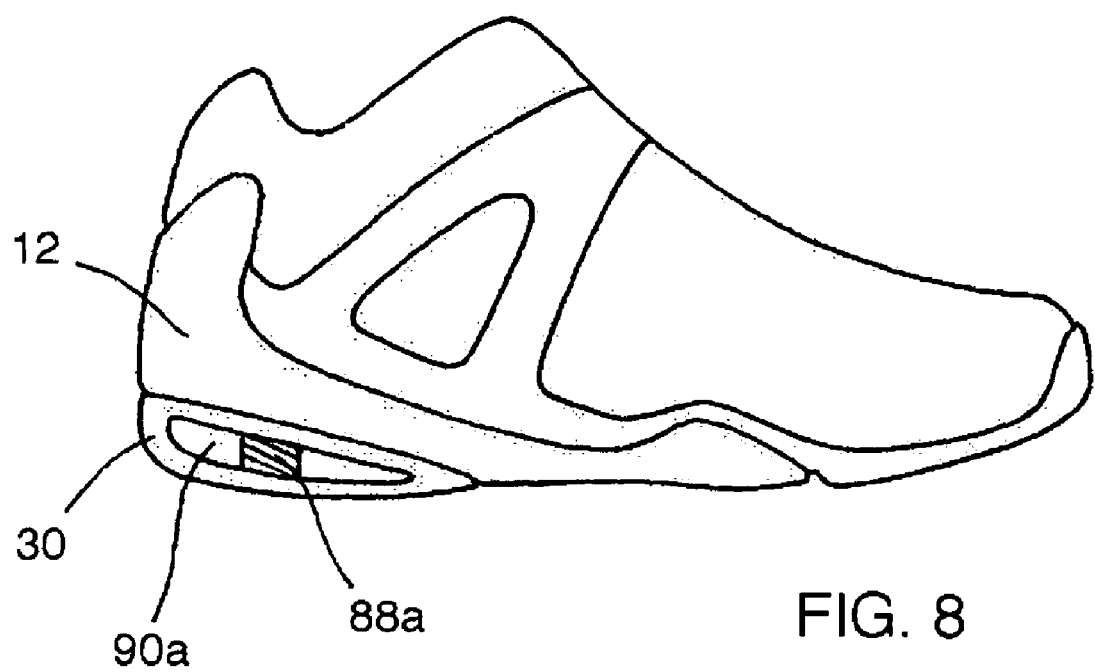
FIG. 8 is a side elevational view of an alternative embodiment of an athletic shoe in which a rear heel cushioning system is configured with additional spring supports located on opposite sides of a multi-level heel.

FIG. 8 illustrates an outer side view of an alternative embodiment of the athletic shoe in which the rear heel cushioning system 30 includes additional spring supports 88a and 88b located on opposite sides of the multi-level heel 74. As shown, the rear heel cushioning system 30 is positioned just below the ankle and heel stabilizing and forefoot torque control member 12. The rear heel cushioning system 30 can be attached to the ankle and heel stabilizing and forefoot torque control member 12 by gluing, for example. As further illustrated, in this embodiment, the rear heel cushioning system 30 is equipped with two apertures 90a and 90b, one located on the inner side of the shoe and one located on the outer side of the shoe. It is understood that FIG. 8 only illustrates the aperture 90a on one side of the shoe but an identical aperture 90b is located within the rear heel cushioning system 30, on the opposite side of the shoe. Each of the apertures 90a and 90b is fitted with a small spring 88a and 88b, respectively, coupled from the top of the aperture 90a and 90b, respectively, to the bottom of the aperture 90a and 90b, respectively. In a preferred embodiment, the springs 88a and 88b are formed of a sturdy resilient metal such as spring steel, titanium or even a synthetic resilient plastic. These springs 88a and 88b help act as shock absorbers and prevent deformity of the multi-level heel 74 when downward pressure is exerted at the heel of the foot. Moreover, the resilience of the springs 88a and 88b provides a certain amount of "bounce" or returned energy to the user if the shoe is worn while running or jumping.

FIG. 2 shows a cutaway of the athletic shoe showing the forefoot cushioning system located in the interior of the shoe. The forefoot cushioning system is comprised of the single cantilever-like molded insole 98 and the double cantilever-like molded midsole 100. As shown, the single cantilever-like molded insole is located above the double cantilever-like molded midsole. FIG. 9A illustrates a lateral view of the single cantilever-like molded insole, which has a physical depression 102 located at approximately the ball of the foot in order to substantially reduce pressure at the ball of the foot. FIG. 9B shows the cross-section of the insole of FIG. 9A through A—A. As shown, the insole may taper slightly from the ball of the foot through the toe. FIG. 10A illustrates a lateral view of the double cantilever-like molded midsole having a top physical depression 104 and a bottom physical depression 106 located at approximately the ball of the foot in order to substantially reduce pressure at the ball of the foot. FIG. 10B shows the cross-section of the midsole of FIG. 10A through B—B. FIG. 10C illustrates a top view of the midsole showing the approximate location of the human foot in relation to the depression(s) of the midsole. FIG. 11 shows an alternative embodiment of the midsole having a single physical depression 108 on the top of the midsole. It is understood that the depressions may have any alternate shape.

In the preferred embodiment, the shoe has a tongue in the upper portion of the shoe under the bridge or top of the shoe. The shoe does not need laces to function properly. A tread is located on the bottom of the shoe to prevent slipping by the wearer. The tread may include grooves or ridges, for example.

In an alternative embodiment, a sock may be used instead of a shoe, giving the wearer the option of wearing a different shoe, while preventing excessive pronation and supination by using the sock. Referring to FIGS. 12A–12C, there is shown an outer side view of the right of an athletic sock of the present invention, an inner side view, and a bottom view, respectively. The sock may be made of any common sock material, including, for example, cotton, polyester, and lycra. The supinator strap 10 operates and functions in the sock in a similar manner as in the shoe. The supinator strap may be made of an elastomer. The supinator strap may be sewn or glued onto the fabric of the sock, or it may be removably attached to the sock with velcro, or it may attached to the sock using any other common mechanism for attachment. The supinator strap is attached with velcro 96 or other methods to the bottom sock near the inner side of the sock and extends around the inner side of the sock and over the bridge or top of the sock toward the outer side of the sock and around the heel of the sock toward the inner side of the sock. The supinator strap extends from the inner side of the sock around the top of the sock toward the lateral heel where it may be removably attached to the sock with velcro 92 or other methods. It further extends around the heel toward the inner side of the sock where it attaches to itself with velcro 94 or other methods.

In an alternative embodiment, a brace may be used instead of a sock, giving the wearer more support. Referring to FIGS. 13A–13C, there is shown an outer side view of the right of a brace of the present invention, an inner side view, and a bottom view, respectively. The brace may be made of any common brace material, including, for example, canvas, nylon, or any other sturdy material. The brace may have laces or velcro to attach the brace to the foot. The supinator strap 10 operates and functions in the same manner in the brace as in the sock. The supinator strap may be made of nylon or canvas.

The foregoing detailed description of the present invention is provided for the purposes of illustration and is not intended to be exhaustive or to limit the invention to the precise embodiment(s) disclosed. Several features of the invention have been described in connection with the disclosed embodiment(s), and these features provide different capabilities and benefits and may be used in different combinations and configurations in the practice of the invention. Accordingly, the scope of the present invention is defined by the following claims.

What is claimed is:

1. An athletic shoe comprising:
   a composite outsole;
   a main body formed on said composite outsole to create an interior shoe cavity having a bottom, the main body having a toe end, a heel end, an instep portion, an ankle portion, and an arch area in which a recess is formed for inserting a foot into the interior shoe cavity; and
   a supinator strap which extends from the bottom of the interior shoe cavity, continues in and around the arch area, and splits into at least two extensions that extend over the instep portion in at least two different directions, in order to provide support and prevent injuries when the shoe is worn.

2. An athletic shoe of claim 1, wherein the supinator strap comprises:
   an arch support band that extends from the bottom of the interior shoe cavity, continues in and around the arch area, continues around an inner side of the shoe, and splits into at least two extensions that extend over the instep portion and toward an outer side of the shoe;

a rear ankle support band that extends from the arch support band on the inner side of the shoe, around the back of the heel end of the main body and toward the outer side of the shoe.

3. An athletic shoe of claim 2, wherein the arch support band is adjustable.

4. An athletic shoe of claim 2, wherein the rear ankle support band is adjustable.

5. An athletic shoe having an outer side and an inner side, the athletic shoe comprising:

a composite outsole;

a main body formed on said composite outsole to create an interior shoe cavity having a bottom, the main body having a toe and, a heel area, a top portion, an ankle portion, and an arch area in which a recess is formed for inserting a foot into the interior shoe cavity, a rear heel cushioning system;

a heel stabilizing and forefoot torque control member positioned above the rear heel cushioning system and extending along the length of the athletic shoe from just behind the ball of the foot to the heel area and up around the ankle portion, said heel stabilizing and forefoot torque control member having at least one fastening slot which extends vertically and which is visible on the outer side of the athletic shoe;

a supinator strap which extends from the bottom of the interior shoe cavity, in and around the arch area, and over the main body in two different directions, in order to provide support and prevent injuries when the shoe is worn, wherein the supinator strap comprises:

an adjustable arch support band that extends from the bottom of the interior shoe cavity, in and around the arch area, wound the inner side of the shoe, over the ton portion of the main body and toward the outer side of the shoe; and a rear ankle support band that extends from the adjustable arch support band on the inner side of the shoe, around the back of the heel end of the main body and toward the outer side of the shoe.

6. An athletic shoe of claim 5, wherein the adjustable arch support band of the supinator strap extends through said at least one fastening slot and folds over onto itself for secure fastening.

7. An athletic shoe of claim 5, wherein the heel stabilizing and forefoot torque control member is formed of durable plastic.

8. An athletic shoe of claim 5, wherein the rear heel cushioning system includes a multi-level heel comprised of:

a cantilever-designed molded outsole; and an external heel cushion positioned between the heel stabilizing and forefoot torque control member and the cantilever-designed molded outsole.

9. An athletic shoe of claim 8, further comprising a forefoot cushioning system, wherein the cushioning system includes at least one insole having at least one depression at the ball of the foot and at least one midsole having at least one depression at the ball of the foot.

10. An athletic shoe of claim 8, wherein both the cantilever-designed molded outsole and the external heel cushion have a centrally located elevated cavern, thereby forming a dome-shaped hollow cavity at the center of the rear multi-level heel.

11. An athletic shoe of claim 10, further comprising a bridge support coupled to opposite sides of the dome-shaped hollow cavity and traversing the entire span of the dome-shaped hollow cavity.

12. An athletic shoe of claim 11, wherein the bridge support is comprised of a natural or synthetic rubber material having lower elasticity than the rest of the individual components in the multi-level heel, such that it holds the dome-shaped hollow cavity together from opposite sides and prevents deformity of the multi-level heel when downward pressure is exerted at the heel of the foot.

13. An athletic shoe of claim 8, wherein the rear heel cushioning system further includes additional spring supports located on opposite sides of the multi-level heel and designed to provide further flexibility and a returned energy when the shoe is worn while running or jumping.

14. An athletic shoe of claim 5, further comprising a forefoot cushioning system, wherein the cushioning system includes at least one insole having at least one depression at the ball of the foot and at least one midsole having at least one depression at the ball of the foot.

15. An athletic shoe comprising:

a composite outsole;

a main body formed on said composite outsole, thereby creating an interior shoe cavity, having a bottom, the main body having a toe end, a heel end, a top portion, an ankle portion, and an arch area in which a recess is formed for inserting a foot into said shoe;

a rear heel cushioning system; and a heel stabilizing and forefoot torque control member positioned above the rear heel cushioning system and extending along the length of the athletic shoe from just behind the ball of the foot to the heel end and encircling the ankle portion.

16. An athletic shoe of claim 15, wherein the heel stabilizing and forefoot torque control member is formed of durable plastic.

17. An athletic shoe of claim 15, wherein the rear heel cushioning system is comprised of a multi-level heel having:

cantilever-designed molded outsole; and an external heel cushion positioned between the heel stabilizing and forefoot torque control member and the cantilever-designed molded outsole.

18. An athletic shoe of claim 17, wherein both the cantilever-designed molded outsole and the external heel cushion have a centrally located elevated cavern, thereby forming a dome-shaped hollow cavity at the center of the rear multi-level heel.

19. An athletic shoe of claim 18, further comprising a bridge support coupled to opposite sides of the dome-shaped hollow cavity and traversing the entire span of the dome-shaped hollow cavity.

20. An athletic shoe of claim 19, wherein the bridge support is comprised of a natural or synthetic rubber material having lower elasticity than the rest of the individual components in the multi-level heel, such that it holds the dome-shaped hollow cavity together from opposite sides and prevents deformity of the multi-level heel when downward pressure is exerted at the heel of the foot.

21. An athletic shoe of claim 17, wherein the rear heel cushioning system further includes additional spring supports located on opposite sides of the multi-level heel and is designed to provide further flexibility and a returned energy when the shoe is worn while running or jumping.

22. An athletic shoe of claim 15, further comprising a supinator strap having:

an arch support band that extends from the bottom of the interior shoe cavity, in and around the arch area, around an inner side of the shoe, over the top portion of the main body and toward an outer side of the shoe; and a rear ankle support band that extends from the arch support band on the inner side of the shoe, around the back of the heel end of the main body and toward the outer side of the shoe.

23. An athletic shoe of claim 15, wherein said heel stabilizing and forefoot torque control member includes at least one fastening slot that extends vertically and which is visible on the outer side of the athletic shoe.

24. An athletic shoe of claim 23, further comprising an adjustable arch support band that pulls up on the arch of the foot.

25. An athletic shoe of claim 23, further comprising an arch support band that pulls up on the arch of the foot, the arch support band extending over the top portion of the athletic shoe, continuing through said at least one fastening slot, and folding over onto itself for secure fastening.

26. An athletic shoe of claim 15, further comprising a forefoot cushioning system, wherein the cushioning system includes at least one insole having at least one depression at the ball of the foot and at least one midsole having at least one depression at the ball of the foot.

27. An athletic shoe of claim 17, further comprising a forefoot cushioning system, wherein the cushioning system includes at least one insole having at least one depression at the ball of the foot and at least one midsole having at least one depression at the ball of the foot.

28. An athletic shoe having an outer side and an inner side, the athletic shoe comprising:
   a composite outsole;
   a main body formed on said composite outsole, thereby creating an interior shoe cavity having a bottom, the main body having a toe end, a heel end, a top portion, an ankle portion, and an arch area in which a recess is formed for inserting a foot into said shoe;
   a rear heel cushioning system;
   a heel stabilizing and forefoot torque control member positioned above the rear heel cushioning system and extending along the length of the athletic shoe from just behind the ball of the foot to the heel end and up around the ankle portion; and a supinator strap having;

an arch support band that extends from the bottom of the interior shoe cavity, in and around the arch area, around the inner side of the shoe, over the top portion of the main body and toward the outer side of the shoe; and a rear ankle support band that extends from the arch support band on the inner side of the shoe, around the back of the heel end of the main body and toward the outer side of the shoe.

29. An athletic shoe comprising:

a composite outsole;

a main body formed on said composite outsole, thereby creating an interior shoe cavity having a bottom, the main body having a toe end, a heel end, a top portion, an ankle portion, and an arch area in which a recess is formed for inserting a foot into said shoe;

a rear heel cushioning system; and a heel stabilizing and forefoot torque control member positioned above the rear heel cushioning system and extending along the length of the athletic shoe from just behind the ball of the foot to the heel end and up round the ankle portion;

wherein the rear heel cushioning system is comprised of a multi-level heel having:

a cantilever-designed molded outsole; and an external heel cushion positioned between the heel stabilizing and forefoot torque control member and the cantilever-designed molded outsole;

wherein the rear heel cushioning system further includes spring supports located on opposite sides of the multi-level heel and designed to provide further flexibility and a returned energy when the shoe is worn while running or jumping.

* * * * *

UNITED STATES PATENT AND TRADEMARK OFFICE
CERTIFICATE OF CORRECTION

PATENT NO. : 7,243,444 B2 Page 1 of 1
APPLICATION NO. : 10/865290
DATED : July 17, 2007
INVENTOR(S) : Marc Selner It is certified that error appears in the above-identified patent and that said Letters Patent is hereby corrected as shown below:

In Detailed Description of Preferred Embodiments, column 8, line 65, please change ";" to --,--
In claim 5, column 13, line 17, please change "and" to --end--
In claim 5, column 13, line 19, please change "," to --;--
In claim 5, column 13, line 37, please change "wound" to --around--
In claim 5, column 13, line 37, please change "ton" to --top--
In claim 17, column 14, line 41, please add "a" before "cantilever-designed"
In claim 21, column 14, line 65, please change "worm" to --worn--
In claim 28, column 16, line 4, please change ":" to --;--
In claim 29, column 16, line 26, please change "round" to --around--

Signed and Sealed this

Twenty-eighth Day of August, 2007

JON W. DUDAS
*Director of the United States Patent and Trademark Office*